US005494896A

United States Patent [19]
Hansbrough

[11] Patent Number: 5,494,896
[45] Date of Patent: Feb. 27, 1996

[54] METHOD OF TREATING CONDITIONS ASSOCIATED WITH BURN INJURIES

[75] Inventor: John F. Hansbrough, Rancho Santa Fe, Calif.

[73] Assignee: XOMA Corporation, Berkeley, Calif.

[21] Appl. No.: 414,924

[22] Filed: Mar. 31, 1995

[51] Int. Cl.$^6$ .......................... A61K 38/16; A61K 38/17; C07K 14/435; C07K 14/47
[52] U.S. Cl. ............................. 514/12; 514/21; 530/350; 424/DIG. 13
[58] Field of Search ........................... 530/350, 827–829; 514/12, 21; 424/78.06, DIG. 13

[56] References Cited

U.S. PATENT DOCUMENTS

| | | | |
|---|---|---|---|
| 5,089,274 | 2/1992 | Marar et al. | 424/534 |
| 5,171,739 | 2/1992 | Scott | 514/12 |
| 5,198,541 | 3/1993 | Elsbach et al. | 435/69.1 |
| 5,234,912 | 8/1993 | Marra et al. | 514/21 |
| 5,308,834 | 5/1994 | Scott et al. | 514/12 |
| 5,334,584 | 8/1994 | Scott et al. | 514/12 |
| 5,348,942 | 9/1994 | Little, II et al. | 514/12 |

FOREIGN PATENT DOCUMENTS

| | | |
|---|---|---|
| WO92/03535 | 3/1992 | WIPO . |
| WO92/09621 | 6/1992 | WIPO . |
| WO93/05797 | 4/1993 | WIPO . |
| WO93/06228 | 4/1993 | WIPO . |
| WO93/23434 | 11/1993 | WIPO . |
| WO93/23540 | 11/1993 | WIPO . |
| WO94/17819 | 8/1994 | WIPO . |
| WO94/18323 | 8/1994 | WIPO . |
| WO94/20128 | 9/1994 | WIPO . |
| WO94/20129 | 9/1994 | WIPO . |

OTHER PUBLICATIONS

Ammons et al., "Recombinant Amino Terminal Fragment of Bactericidal/Permeability–Increasing Protein Prevents Hemodynamic Responses to Endotoxin", *Circulatory Shock,* 41:176–184 (1993).

Ammons et al., Annual Meeting of Professional Scientific Research Scientists, Experimental Biology 94, Anaheim, California, Abstracts 1–3391, Part I, Ischemic Injury, 753 (Apr. 24–28, 1994).

Botha et al., "Postinjury Neutrophil Priming and Activation States: Therapeutic Challenges", *Shock,* 157–166 (1995).

Casey et al., "Plasma Cytokine and Endotoxin Levels Correlate with Survival in Patients with the Sepsis Syndrome", *Annals Internal Med.* 119:771–778 and 853–854 (1993).

Cioffi et al., "Leukocyte Responses to Injury", *Arch Surg.,* 128: 1260–1267 (1993).

De Bandt et al., "Cytokine Response to Burn Injury: Relationship with Protein Metabolism", *J. Trauma,* 36:624–628 (1994).

Elsbach and Weiss, "Oxygen–Independent Bactericidal Systems of Polymorphonuclear Leukocytes", in *Advance in Inflammation Research,* vol. 2, pp. 95–113 (Weissman ed., Raven Press, Ltd.) (1981).

Elsbach and Weiss, "Oxygen–Independent Antimicrobial Systems of Phagocytes", in *Inflammation: Basic Principles And Clinical Correlates,* pp. 603–636, (Gallin et al., eds., Raven Press. Ltd.) (1992).

Elsbach et al., "Separation and Purification of a Potent Bactericidal/Permeability–Increasing Protein and a Closely Associated Phospholipase A$_2$ from Rabbit Polymorphonuclear Leukocytes", *J. Biol. Chem.,* 254(21):11000–11009 (Nov. 10, 1979).

Gamelli et al., "Marrow Granulocyte–Macrophage Progenitor Cell Response to Burn Injury as Modified by Endotoxin and Indomethacin", *J. Trauma,* 37:339–346 (1994).

Gazzano–Santoro et al. "High–Affinity Binding of the Bactericidal/Permeability–Increasing Protein and a Recombinant Amino–Terminal Fragment to the Lipid A Region of Lipopolysaccharide", *Infect. Immun.* 60(11):4754–4761 (Nov. 1992).

Gray et al., "Cloning of the cDNA of a Human Neutrophil Bactericidal Protein", *J. Biol. Chem.,* 264(16):9505–9509 (Jun. 5, 1989).

Hansbrough et al., "Critical Decisions", *Problems in Critical Care,* 1(4):588–610 (1987).

In't Veld et al., "Effects of the Bactericidal/ Permeability–Increasing Protein of Polymorphonuclear Leukocytes on Isolated Bacterial Cytoplasmic Membrane Vesicles", *Infect. and Immun.* 56(5):1203–1208 (May 1988).

Kelly et al., "Role of bactericidal permeability–increasing protein in the treatment of gram–negative pneumonia", *Surgery,* 114:140–146 (Aug. 1993).

Kohn et al., "Protective Effect of a Recombinant Amino–Terminal Fragment of Bactericidal/ Permeability–Increasing Protein in Experimental Endotoxemia", *J. Infections Diseases,* 168:1307–1310 (1993).

Koike et al., "Gut ischemia/reperfusion produces lung injury independent of endotoxin", *Critical Care Med.,* 22: 1438–1443 (1994).

Kung et al., *Bacterial Endotoxins: Basic Science to Anti–Sepsis Strategies,* Wiley–Liss, New York, pp. 255–263 (1994).

Kung, et al., "In Vivo Efficacy Evaluation of rBPI$_{23}$ in Animals Challenged with Live Bacteria", International Conference on Endotoxin IV, Amsterdam, Netherlands, Aug. 17–20, 1993 (Abstract 022).

Leach et al., "Recognition of Endotoxin in Biologic Systems", Keystone Symposia, Lake Tahoe, Calif., Mar. 1–7, 1992. (Abstract).

Mainous et al., "Bacterial Translocation", in *Pathophysiology of Shock, Sepsis, and Organ Failure,* Springer–Verlag, Berlin, pp. 265–278 (1993).

Mannion et al., "Separation of Sublethal and Lethal Effects (List continued on next page.)

*Primary Examiner*—Christina Y. Chan
*Assistant Examiner*—Nancy J. Degen
*Attorney, Agent, or Firm*—Marshall, O'Toole, Gerstein, Murray & Borun

[57] ABSTRACT

The present invention provides methods of preventing or treating conditions associated with burn injuries by administering bactericidal/permeability-increasing (BPI) protein product.

10 Claims, No Drawings

OTHER PUBLICATIONS of the Bactericidal/Permeability Increasing Protein on *Escherichia coli*", *J. Clin. Invest.*, 85:853–860 (Mar. 1990).

Mannion et al., "Separation of Sublethal and Lethal Effects of Polymorphonuclear Leukocytes on *Escherichia coli*", *J. Clin. Invest.* 86:631–641 (Aug. 1990).

Marano et al., "Serum Cachectic/Tumor Necrosis Factor in Critically Ill Patients with Burns Correlates with Infection and Mortality", *Surgery, Gynecology & Obstetrics*, 170:32–38 (1990).

Marra et al., *J. Immunol.*, "Bactericidal/Permeability–Increasing Protein Has Endotoxin–Neutralizing Activity", *J. Immunol*, 144(2):662–666 (Jan. 15, 1990).

Marra et al., *J. Immunol.*, "The Role of Bactericidal/Permeability–increasing Protein as a Natural Inhibitor of Bacterial Endotoxin", *J. Immunol.*, 148(2):532–537 (Jan. 15, 1992).

Marra et al., "Endotoxin–binding and –neutralizing properties of recombinant bactericidal/permeability–increasing protein and monoclonal antibodies HA–1A and E5", *Critical Care Med.*, 22(4):559–565 (1994).

Meade et al., "Termporal Patterns of Hemodynamics, Oxygen Transport, Cytokine Activity, and Complement Activity in the Development of Adult Respiratory Distress Syndrome After Severe Injury", *J. Trauma*, 36:651–657 (1994).

Mulligan et al., "Role of Leukocyte Adhesion Molecules in Lung and Dermal Vascular Injury after Thermal Trauma of Skin", *Am. J. Pathol.*, 144:1008–1015 (1994).

Ooi et al., "Endotoxin–neutralizing Properties of the 25 kD N–Terminal Fragment and of the 55–60 kD Bactericidal/Permeability–Increasing Protein of Human Neutrophils", *J. Exp. Med.*, 174:649–655 (Sep. 1991).

Ooi et al., "A 25–kDa $NH_2$–terminal Fragment Carries All the Antibacterial Activities of the Human Neutrophil 60–kDa Bactericidal/Permeability–Increasing Protein", *J. Bio. Chem.*, 262(31):14891–14894 (1987).

Rennekampff et al., "Bactericidal/Permeability–Increasing Protein (rBPI23) Reduces Bactericidal Translocation After Burn Injury", *Proc. Am. Burn Assoc.*, 27th Annual Meeting Albuquerque, N. Mex. (Apr. 19–22, 1995).

Rodriguez et al., "Correlation of the Local and Systemic Cytokine Response with Clinical Outcome following Thermal Injury", *J. Trauma*, 34:684–695 (1993).

Ryan et al., "Additive Effects of Thermal Injury and Infection on Gut Permeability", *Arch. Surg.*, 129:325–328 (1994).

Suzuki et al., "Interleukin 1 and Tumor Necrosis Factor Production as the Initial Stimulants of Liver Ischemia and Reperfusion Injury", *J. Surg. Res.*, 57:253–258 (1994).

Von der Mohlen et al., "Protection from endotoxin–induced cytokine response and neutrophil activation in human by $rBPI_{23}$", 34th Interscience Conference on Antimicrobial Agents and Chemotherapy, Orlando, Florida, Oct. 4–7, 1994.

Von der Mohlen et al., "Inhibition of Many Inflammatory Responses in Experimental Endotoxemia in Human Volunteers by $rBPI_{23}$", 34th Interscience Conference on Antimicrobial Agents and Chemotherapy, Orlando, Florida, Oct. 4–7, 1994.

Von der Mohlen et al., "Effect of $rBPI_{23}$ on Endotoxin–Induced Cytokine Release and Leukocyte Changes in Human Volunteers", *Clin. Res.*, 42: 152A (1994).

Weiss et al., "Resistance of Gram–negative Bacteria to Purified Bactericidal Leukocyte Proteins", *J. Clin. Invest.*, 65:619–628 (Mar. 1980).

Weiss et al., "The Role of Lipopolysaccharides in the Action of the Bactericidal/Permeability–Increasing Neutrophil Protein on the Bacterial Envelope", *J. Immunol.* 132(6):3109–3115 (Jun. 1984).

Weiss and Olsson, "Cellular and Subcellular Localization of the Bactericidal/Permeability–Increasing Protein of Neutrophils", *Blood*, 69(2):652–659 (Feb. 1987).

METHOD OF TREATING CONDITIONS ASSOCIATED WITH BURN INJURIES

BACKGROUND OF THE INVENTION

The present invention relates generally to methods of treating patients suffering from conditions associated with or resulting from burn injuries by administration of bactericidal/permeability-increasing (BPI) protein products.

Burn trauma causes approximately two million injuries, 100,000 hospital admissions, and 10,000 deaths every year in the United States. [Marano et al., *Surgery, Gynecology & Obstetrics,* 170:32–38 (1990).] In the past, many victims did not survive the initial resuscitation period. Current survival rates and clinical outcomes have progressively improved with the advent of aggressive burn wound excision techniques, graft therapy, and superior intensive care facilities, along with a better understanding of postburn physiological factors and fluid requirements, but further improvements are needed. Currently, patient morbidity and mortality is associated largely with pulmonary infection and inflammatory lung disease, such as adult respiratory distress syndrome (ARDS). Pulmonary problems occur most often in patients with extensive cutaneous burns, patients with associated smoke inhalation injury, and the elderly.

Current therapy, for example, at a regional burn center, involves immediate treatment of the patient with burn injuries, focusing on maintaining the airway, breathing and circulation. Placement of an endotracheal tube and respiratory support using controlled ventilation may be necessary. Typically, intravenous lines are placed immediately to permit fluid resuscitation to treat burn shock, which occurs generally in patients with burns over 20% of the total body surface area (TBSA), and is exacerbated in the elderly and those with smoke inhalation injury to the lungs. Fluid resuscitation continues for approximately 24 hours following burn injury, the period of severe capillary permeability. Generally, during this time the patient is carefully monitored and fluid administration rates are adjusted to achieve optimal tissue and organ perfusion. Severe burns require the administration of colloids (protein solutions) since large amounts of plasma protein may leak into the interstitial tissue secondary to the capillary leak. Prophylactic antibiotics are generally not used for burns, since resistant organisms will rapidly be selected. Rather, serial samples from the patient (primarily the wounds and the lungs) are taken and cultured and treatment of suspected infections is based on the results of surveillance cultures and the identity of common microorganisms which may be endemic in the individual burn unit. Nutritional support is typically initiated as early as possible, preferably with enteral administration of high-protein diets. Intravenous (parenteral) alimentation is avoided in burn patients since it is associated with very high complication rates and does not support the gastrointestinal tract.

After initiation of such supportive treatment, current therapy involves debriding wounds of loose epithelium. Topical antimicrobial agents, usually silver sulfadiazine, are applied to the open wounds. Partial-thickness burns which are expected to heal are treated with daily debridements and continuation of topical antimicrobial agents. Burn wounds which are full-thickness or deep partial-thickness are considered for surgical excisional therapy, which is normally begun within several days, as soon as the patient is stable. Wound excision is followed by coverage of the open wounds with the patient's own skin (autograft) or with a temporary skin substitute, usually cadaver allograft, if the wounds are very extensive or if the patient is unstable. Temporary skin replacements are eventually replaced with autografts.

Acute burn injury initiates an early cytokine response in patients that involves tumor necrosis factor (TNF), interleukin-6 (IL-6) and interleukin-8 (IL-8). These cytokines are elevated in plasma and in local organs, including lung and skin. The cytokine responses in the lung and skin appear to be generated locally and do not originate from the systemic cytokine pool; local cytokine responses thus may play a greater role in local organ failure than the systemic response. Increased severity of burn injury or direct injury to the lung corresponds to increased systemic IL-8 levels, but not TNF or IL-6 levels. [Rodriguez et al., *J. Trauma,* 34:684–695 (1993).] TNF levels are detectable with greater frequency and at higher concentrations in burn patients with sepsis or a fatal outcome, but do not appear to correlate with the extent of burn injury. [Marano et al., *supra*; De Bandt et al., *J. Trauma,* 36:624–628 (1994).] One report has shown a correlation between elevated IL-6 levels postburn and the extent of burn injury. [De Bandt et al., *supra*.]

The inflammatory response and release of mediators that is associated with burn injury often results in vascular injury (increased permeability and hemorrhage) and tissue injury in the skin and in remote organs such as the lung. This vascular and tissue injury has been shown to be neutrophil-dependent. [Mulligan et al., *Am. J. Pathol.,* 144:1008–1015 (1994).] Neutrophils respond to the systemic inflammation that initially follows major trauma by becoming primed and activated. Subsequent proinflammatory insults promote neutrophil deposition in tissues (leukosequestration) and release of proteases and oxygen metabolites from the sequestered neutrophils. The resulting vascular and tissue injury may lead to a self-sustaining cycle of neutrophil sequestration, additional vascular and tissue injury, and eventual end organ damage and failure. [Botha et al., *Shock,* 3:157–166 (1995).]

BPI is a protein isolated from the granules of mammalian polymorphonuclear leukocytes (PMNs or neutrophils), which are blood cells essential in the defense against invading microorganisms. Human BPI protein has been isolated from PMNs by acid extraction combined with either ion exchange chromatography [Elsbach, *J. Biol. Chem.,* 254:11000 (1979)] or *E. coli* affinity chromatography [Weiss, et al., *Blood,* 69:652 (1987)]. BPI obtained in such a manner is referred to herein as natural BPI and has been shown to have potent bactericidal activity against a broad spectrum of gram-negative bacteria. The molecular weight of human BPI is approximately 55,000 daltons (55 kD). The amino acid sequence of the entire human BPI protein and the nucleic acid sequence of DNA encoding the protein have been reported in FIG. 1 of Gray et al., *J. Biol. Chem.,* 264:9505 (1989), incorporated herein by reference. The Gray et al. amino acid sequence is set out in SEQ ID NO: 1 hereto.

BPI is a strongly cationic protein. The N-terminal half of BPI accounts for the high net positive charge; the C-terminal half of the molecule has a net charge of −3. [Elsbach and Weiss (1981), *supra*.] A proteolytic N-terminal fragment of BPI having a molecular weight of about 25 kD has an amphipathic character, containing alternating hydrophobic and hydrophilic regions. This N-terminal fragment of human BPI possesses the anti-bacterial efficacy of the naturally-derived 55 kD human BPI holoprotein. [Ooi et al., *J. Bio. Chem.,* 262:14891–14894 (1987)]. In contrast to the N-terminal portion, the C-terminal region of the isolated human BPI protein displays only slightly detectable anti-bacterial activity against gram-negative organisms. [Ooi et al., *J. Exp. Med.*, 174:649 (1991).] An N-terminal BPI fragment of approximately 23 kD, referred to as "rBPI$_{23}$," has been produced by recombinant means and also retains antibacterial activity against gram-negative organisms. Gazzano-Santoro et al., *Infect. Immun.* 60:4754–4761 (1992).

The bactericidal effect of BPI has been reported to be highly specific to gram-negative species, e.g., in Elsbach and Weiss, *Inflammation: Basic Principles and Clinical Correlates*, eds. Gallin et al., Chapter 30, Raven Press, Ltd. (1992). This reported target cell specificity was believed to be the result of the strong attraction of BPI for lipopolysaccharide (LPS), which is unique to the outer membrane (or envelope) of gram-negative organisms.

The precise mechanism by which BPI kills gram-negative bacteria is not yet completely elucidated, but it is believed that BPI must first bind to the surface of the bacteria through electrostatic and hydrophobic interactions between the cationic BPI protein and negatively charged sites on LPS. LPS has been referred to as "endotoxin" because of the potent inflammatory response that it stimulates, i.e., the release of mediators by host inflammatory cells which may ultimately result in irreversible endotoxic shock. BPI binds to lipid A, reported to be the most toxic and most biologically active component of LPS.

In susceptible gram-negative bacteria, BPI binding is thought to disrupt LPS structure, leading to activation of bacterial enzymes that degrade phospholipids and peptidoglycans, altering the permeability of the cell's outer membrane, and initiating events that ultimately lead to cell death. [Elsbach and Weiss (1992), *supra*]. BPI is thought to act in two stages. The first is a sublethal stage that is characterized by immediate growth arrest, permeabilization of the outer membrane and selective activation of bacterial enzymes that hydrolyze phospholipids and peptidoglycans. Bacteria at this stage can be rescued by growth in serum albumin supplemented media [Mannion et al., *J. Clin. Invest.*, 85:853–860 (1990)]. The second stage, defined by growth inhibition that cannot be reversed by serum albumin, occurs after prolonged exposure of the bacteria to BPI and is characterized by extensive physiologic and structural changes, including apparent damage to the inner cytoplasmic membrane.

Initial binding of BPI to LPS leads to organizational changes that probably result from binding to the anionic groups in the KDO region of LPS, which normally stabilize the outer membrane through binding of Mg$^{++}$ and Ca$^{++}$. Attachment of BPI to the outer membrane of gram-negative bacteria produces rapid permeabilization of the outer membrane to hydrophobic agents such as actinomycin D. Binding of BPI and subsequent gram-negative bacterial killing depends, at least in part, upon the LPS polysaccharide chain length, with long O-chain bearing, "smooth" organisms being more resistant to BPI bactericidal effects than short O-chain bearing, "rough" organisms [Weiss et al., *J. Clin. Invest.* 65:619–628 (1980)]. This first stage of BPI action, permeabilization of the gram-negative outer envelope, is reversible upon dissociation of the BPI, a process requiring the presence of divalent cations and synthesis of new LPS [Weiss et al., *J. Immunol.* 132: 3109–3115 (1984)]. Loss of gram-negative bacterial viability, however, is not reversed by processes which restore the envelope integrity, suggesting that the bactericidal action is mediated by additional lesions induced in the target organism and which may be situated at the cytoplasmic membrane (Mannion et al., *J. Clin. Invest.* 86: 631–641 (1990)). Specific investigation of this possibility has shown that on a molar basis BPI is at least as inhibitory of cytoplasmic membrane vesicle function as polymyxin B (In't Veld et al., *Infection and Immunity* 56:1203–1208 (1988)) but the exact mechanism as well as the relevance of such vesicles to studies of intact organisms has not yet been elucidated.

Of interest to the background of the present invention are reports of interaction between bacterial endotoxin and BPI protein products in various in vitro and non-human in vivo assay systems. As one example, Leach et al., Keystone Symposia "Recognition of Endotoxin in Biologic Systems", Lake Tahoe, Calif., Mar. 1–7, 1992 (Abstract) reported that rBPI$_{23}$ (as described in Gazzano-Santoro et al., *supra*) prevented lethal endotoxemia in actinomycin D-sensitized CD-1 mice challenged with *E. coli* 011:B4 LPS. In additional studies Kohn et al., *J. Infectious Diseases*, 168:1307–1310 (1993) demonstrated that rBPI$_{23}$ not only protected actinomycin-D sensitized mice in a dose-dependent manner from the lethal effects of LPS challenge but also attenuated the LPS-induced elevation of TNF and IL-1 in serum. Ammons et al., [*Circulatory Shock*, 41:176–184 (1993)] demonstrated in a rat endotoxemia model that rBPI$_{23}$ produced a dose-dependent inhibition of hemodynamic changes associated with endotoxemia. Kelly et al., *Surgery*, 114:140–146 (1993) showed that rBPI$_{23}$ conferred significantly greater protection from death than an antiendotoxin monoclonal antibody (E5) in mice inoculated intratracheally with a lethal dose of *E. coli*. Kung, et al., International Conference on Endotoxin IV, Amsterdam, Netherlands, Aug. 17–20, 1993 (Abstract 022) and in *Bacterial Endotoxins: Basic Science to Anti-Sepsis Strategies*, Wiley-Liss, N.Y., pages 255–263 (1994) disclosed the efficacy of rBPI$_{23}$ in several animal models including live bacterial challenge and endotoxemia models. Von der Mohlen et al., 34th Interscience Conference on Antimicrobial Agents and Chemotherapy, Orlando, Fla. Oct. 4–7, 1994 (Abstract M3), disclosed that rBPI$_{23}$ administration alleviated serological, hematological and hemodynamic effects of endotoxin administration, including blunting the leukocyte response and reducing neutrophil activation.

M. N. Marra and R. W. Scott and co-workers have addressed endotoxin interactions with BPI protein products in U.S. Pat. Nos. 5,089,274 and 5,171,739, in published PCT Application WO 92/03535 and in Marra et al., *J. Immunol.*, 144:662–665 (1990), Marra et al., *J. Immunol.*, 148:532–537 (1992), and Marra et al., *Critical Care Med.*, 22(4):559–565 (1994). In vitro and non-human in vivo experimental procedures reported in these documents include positive assessments of the ability of BPI-containing granulocyte extracts, highly purified granulocytic BPI and recombinant BPI to inhibit endotoxin stimulation of cultures of human adherent mononuclear cells to produce tumor necrosis factor α (TNF) when endotoxin is pre-incubated with the BPI product. Pre-incubation of endotoxin with BPI protein products was also shown to diminish the capacity of endotoxin to stimulate (upregulate) neutrophil cell surface expression of receptors for the complement system components C3b and C3bi in vitro. The experimental studies reported in these documents included in vivo assessments of endotoxin interaction with BPI protein products in test subject mice and rats.

Also of interest to the background of the present invention is a report showing a direct relationship between the extent of burn injury and gut permeability in rats, with additive increases in gut permeability seen in association with *Pseudomonas aeruginosa* infections in the burn wound. See Ryan et al., *Arch. Surg.*, 129:325–328 (1994). Also of interest to the present invention is the report that BPI protein products reduce the adverse physiological effects, including cardiac and hemodynamic alterations, associated with intestinal ischemia/reperfusion injury in rats. See Ammons et al., *Annual Meeting of Professional Scientific Research Scientists, Experimental Biology 94™*, Anaheim, Calif., Abstracts 1-3391, Part I, Ischemic Injury, 753 (Apr. 24–28, 1994).

Of further interest to the present invention is the report that granulocyte and macrophage proliferation is suppressed in burned and infected mice and appears to be related in part to endotoxin-stimulated production of prostaglandin mediators. [Gamelli et al., *J. Trauma*, 37:339–346 (1994).]

There continues to exist a need in the art for new methods and materials for treatment of burn injuries. Products and methods responsive to this need would ideally involve substantially non-toxic compounds available in large quantities by means of synthetic or recombinant methods. Ideal compounds would prevent or reduce the number and severity of complications associated with or resulting from burn injuries, or enhance the effect of other concurrently administered therapeutic agents, such as antibiotics or anti-fungal agents.

SUMMARY OF THE INVENTION

The present invention provides novel methods of preventing or treating conditions associated with or resulting from a burn injury, by administering a therapeutically effective amount of a BPI protein product to a subject suffering from the effects of a burn injury. The invention derives from the surprising discovery that BPI protein products prevent or reduce adverse effects associated with burn injuries, particularly leukosequestration in remote organs and the incidence of bacterial translocation from the gut, as measured by bacterial accumulation in mesenteric lymph nodes. It is also contemplated that the BPI protein product be administered according to the invention concurrently with anti-bacterial and/or anti-fungal agents, including for example antibiotics.

The invention further provides for the use of a BPI protein product for manufacture of a medicament for preventing or treating conditions associated with or resulting from a burn injury, particularly leukosequestration in remote organs and the incidence of bacterial translocation from the gut, as measured by bacterial accumulation in mesenteric lymph nodes.

Numerous additional aspects and advantages of the invention will become apparent to those skilled in the art upon considering the following detailed description of the invention, which describes the presently preferred embodiments thereof.

DETAILED DESCRIPTION OF THE INVENTION

The present invention relates to the surprising discovery that a BPI protein product can be administered to subjects suffering from burn injuries, and conditions associated therewith or resulting therefrom, and provides methods of preventing or treating such conditions. BPI protein products are shown herein to prevent or reduce adverse effects associated with burn injuries, including the amount of postburn leukosequestration in remote organs such as the lung and liver, and the incidence of bacterial translocation from the gut, as measured by bacterial accumulation in mesenteric lymph nodes.

There is evidence that the development of organ dysfunction following injury, sepsis and shock, for example, impaired organ function resulting in adult respiratory distress syndrome (ARDS), is closely related to the accumulation of PMNs in the organs, followed by the local release of toxic mediators including proteases and high energy oxygen metabolites. Priming, adherence and activation of PMNs may be mediated by endotoxin in association with release of multiple cytokines, which may elicit both systemic and local effects. However, the role of endotoxin in leukosequestration and remote organ injury has not been well defined. Sequestration of metabolically active PMNs may induce tissue injury; vascular and tissue injury in locations remote from the burn site have been shown to be neutrophil-dependent. Thus, therapies which block postburn leukosequestration may improve clinical outcomes by limiting remote tissue injury. In addition, therapies which block postburn bacterial translocation from the gut may improve clinical outcome by reducing the exposure to bacteria and their endotoxin products.

BPI protein product may be administered in addition to standard therapy and is preferably incorporated into the initial critical care given the burn patient. The BPI protein product is preferably administered intravenously (e.g., by continuous infusion) to the patient as soon as possible after injury, at the same time as or immediately after fluid resuscitation begins. Patients are administered doses of BPI protein product between about 1 µg/kg to about 100 mg/kg daily, and preferably from about 1 mg/kg to about 20 mg/kg daily. Treatment with BPI protein product is preferably continued for at least one to two days, and potentially longer if necessary. BPI protein product treatment may provide the greatest benefit to patients with severe burns (for example, those with greater than 40% TBSA burn injury) and patients with moderate to severe smoke inhalation injury, but may improve the condition of patients with any degree of burn injury. Improvement of the patient's condition may be monitored over time as measured by preventing or reducing the development of complications and/or mortality. Such complications may include, for example, impaired organ function and infection.

BPI protein products could provide additional benefits by their ability to neutralize circulating endotoxin associated with translocation of gram-negative bacteria and/or concomitant gram-negative bacterial infection in burn patients. BPI protein products could provide further benefits due to their anti-bacterial activity against susceptible bacteria and fungi, and their ability to enhance the therapeutic effectiveness of antibiotics and anti-fungal agents. See, e.g., Horwitz et al., co-owned, co-pending U.S. application Ser. No. 08/372,783, filed Jan. 13, 1995 as a continuation-in-part of U.S. application Ser. No. 08/274,299, filed Jul. 11, 1994, which are all incorporated herein by reference and which describe BPI protein product activity in relation to gram-positive bacteria; and Little et al., co-owned, co-pending U.S. application Ser. No. 08/372,105, filed Jan. 13, 1995 as a continuation-in-part of U.S. application Ser. No. 08/273,540, filed Jul. 11, 1994, which are all incorporated herein by reference and which describe BPI protein product activity in relation to fungi.

The BPI protein product may be administered systemically, or topically to the burn wounds. Systemic routes of administration include oral, intravenous, intramuscular or subcutaneous injection (including into a depot for long-term release), intraocular or retrobulbar, intrathecal, intraperitoneal (e.g. by intraperitoneal lavage), transpulmonary using aerosolized or nebulized drug, or transdermal. Topical routes include administration in the form of salves, ophthalmic drops, ear drops, or irrigation fluids (for, e.g., irrigation of wounds). Those skilled in the art can readily optimize effective dosages and administration regimens for the BPI protein products.

It is also contemplated that the BPI protein product be administered with other products that potentiate the activity of BPI protein products, such as complement, p15 and LBP, other cells and components of the immune system, and poloxamer surfactants. For example, serum complement potentiates the gram-negative anti-bacterial activity of BPI protein products. BPI anti-bacterial activity is also potentiated by 15 kD proteins, designated p15, derived from the granules of rabbit PMNs [see, e.g., Ooi et al. *J. Biol. Chem.*, 265:15956 (1990) and Levy et al. *J. Biol. Chem.*, 268: 6038–6083 (1993)]. Co-owned, co-pending PCT Application No. US94/07834 filed Jul. 13, 1994, which corresponds to U.S. patent application Ser. No. 08/274,373 filed Jul. 11, 1994 as a continuation-in-part of U.S. Pat. application Ser. No. 08/093,201 filed Jul. 14, 1993, which are all incorporated herein by reference, describe methods for potentiating gram-negative bactericidal activity of BPI protein products by administering lipopolysaccharide binding protein (LBP) and LBP protein products. LBP protein derivatives and derivative hybrids which comprise a portion of the amino acid sequence of LBP and which bind to LPS but lack the carboxy terminal-associated CD14-mediated immunostimulatory activity characteristic of the LBP, are described in detail in PCT Application No. US94/06931 filed Jun. 17, 1994, which corresponds to co-owned, co-pending U.S. Pat. application serial No. 08/261,660, filed Jun. 17, 1994 as a continuation-inpart of U.S. patent application Ser. No. 08/079,510, filed Jun. 17, 1993, the disclosures of all of which are incorporated herein by reference. Potentiation of BPI protein product activity by poloxamer surfactants is described in co-owned, co-pending U.S. patent application Ser. No. 08/372,104 filed Jan. 13, 1995, the disclosure of which is incorporated herein by reference.

As used herein, "BPI protein product" includes naturally and recombinantly produced BPI protein; natural, synthetic, and recombinant biologically active polypeptide fragments of BPI protein; biologically active polypeptide variants of BPI protein or fragments thereof, including hybrid fusion proteins and dimers; biologically active polypeptide analogs of BPI protein or fragments or variants thereof, including cysteine-substituted analogs; and BPI-derived peptides. The BPI protein products administered according to this invention may be generated and/or isolated by any means known in the art. U.S. Pat. No. 5,198,541, the disclosure of which is incorporated herein by reference, discloses recombinant genes encoding and methods for expression of BPI proteins including recombinant BPI holoprotein, referred to as rBPI$_{50}$ and recombinant fragments of BPI. Co-owned, copending U.S. patent application Ser. No. 07/885,501 and a continuation-in-part thereof, U.S. patent application Ser. No. 08/072,063 filed May 19, 1993 and corresponding PCT Application No. 93/04752 filed May 19, 1993, which are all incorporated herein by reference, disclose novel methods for the purification of recombinant BPI protein products expressed in and secreted from genetically transformed mammalian host cells in culture and discloses how one may produce large quantities of recombinant BPI products suitable for incorporation into stable, homogeneous pharmaceutical preparations.

Biologically active fragments of BPI (BPI fragments) include biologically active molecules that have the same or similar amino acid sequence as a natural human BPI holoprotein, except that the fragment molecule lacks amino-terminal amino acids, internal amino acids, and/or carboxy-terminal amino acids of the holoprotein. Nonlimiting examples of such fragments include a N-terminal fragment of natural human BPI of approximately 25 kD, described in Ooi et al., *J. Exp. Med.*, 174:649 (1991), and the recombinant expression product of DNA encoding N-terminal amino acids from 1 to about 193 or 199 of natural human BPI, described in Gazzano-Santoro et al., *Infect. Immun.* 60:4754–4761 (1992), and referred to as rBPI$_{23}$. In that publication, an expression vector was used as a source of DNA encoding a recombinant expression product (rBPI$_{23}$) having the 31-residue signal sequence and the first 199 amino acids of the N-terminus of the mature human BPI, as set out in FIG. 1 of Gray et al., *supra*, except that valine at position 151 is specified by GTG rather than GTC and residue 185 is glutamic acid (specified by GAG) rather than lysine (specified by AAG). Recombinant holoprotein (rBPI) has also been produced having the sequence (SEQ ID NOS: 1 and 2) set out in FIG. 1 of Gray et al., *supra*, with the exceptions noted for rBPI$_{23}$ and with the exception that residue 417 is alanine (specified by GCT) rather than valine (specified by GTT). Other examples include dimeric forms of BPI fragments, as described in co-owned and co-pending U.S. patent application Ser. No. 08/212,132, filed Mar. 11, 1994, the disclosures of which are incorporated herein by reference. Preferred dimeric products include dimeric BPI protein products wherein the monomers are amino-terminal BPI fragments having the N-terminal residues from about 1 to 175 to about 1 to 199 of BPI holoprotein. A particularly preferred dimeric product is the dimeric form of the BPI fragment having N-terminal residues 1 through 193, designated rBPI$_{42}$ dimer.

Biologically active variants of BPI (BPI variants) include but are not limited to recombinant hybrid fusion proteins, comprising BPI holoprotein or biologically active fragment thereof and at least a portion of at least one other polypeptide, and dimeric forms of BPI variants. Examples of such hybrid fusion proteins and dimeric forms are described by Theofan et al. in co-owned, copending U.S. patent application Ser. No. 07/885,911, and a continuation-in-part application thereof, U.S. patent application Ser. No. 08/064,693 filed May 19, 1993 and corresponding PCT Application No. US93/04754 filed May 19, 1993, which are all incorporated herein by reference and include hybrid fusion proteins comprising, at the amino-terminal end, a BPI protein or a biologically active fragment thereof and, at the carboxy-terminal end, at least one constant domain of an immunoglobulin heavy chain or allelic variant thereof. Another example of such a hybrid fusion protein is the recombinant expression product of DNA encoding amino acids 1 through 199 of BPI joined to DNA encoding amino acids 198 through 456 of LBP, designated BPI(1–199)-LBP(198–456) hybrid, is described in PCT Application No. US94/06931 filed Jun. 17, 1994, which corresponds to co-owned, co-pending U.S. patent application Ser. No. 08/261,660, filed Jun. 17, 1994 as a continuation-in-part of U.S. patent application Ser. No. 08/079,510, filed Jun. 17, 1993, the disclosures of all of which are incorporated herein by reference.

Biologically active analogs of BPI (BPI analogs) include but are not limited to BPI protein products wherein one or more amino acid residues have been replaced by a different amino acid. For example, co-owned, copending U.S. patent application Ser. No. 08/013,801 filed Feb. 2, 1993 and corresponding PCT Application No. US94/01235 filed Feb. 2, 1994, the disclosures of which are incorporated herein by reference, discloses polypeptide analogs of BPI and BPI fragments wherein a cysteine residue is replaced by a different amino acid. A preferred BPI protein product described by this application is the expression product of DNA encoding from amino acid 1 to approximately 193 or 199 of the N-terminal amino acids of BPI holoprotein, but wherein the cysteine at residue number 132 is substituted with alanine and is designated rBPI$_{21}$Δcys or rBPI$_{21}$. Other examples include dimeric forms of BPI analogs; e.g. co-owned and co-pending U.S. patent application Ser. No. 08/212,132 filed Mar. 11, 1994, the disclosures of which are incorporated herein by reference.

Other BPI protein products useful according to the methods of the invention are peptides derived from or based on BPI produced by synthetic or recombinant means (BPI-derived peptides), such as those described in co-owned and copending PCT Application No. US94/10427 filed Sep. 15, 1994, which corresponds to U.S. patent application Ser. No. 08/306,473 filed Sep. 15, 1994, and PCT Application No. US94/02465 filed Mar. 11, 1994, which corresponds to U.S. patent application Ser. No. 8/209,762, filed Mar. 11, 1994, which is a continuation-in-part of U.S. patent application Ser. No. 08/183,222, filed Jan. 14, 1994, which is a continuation-in-part of U.S. patent application Ser. No. 08/093,202 filed Jul. 15, 1993 (for which the corresponding international application is PCT Application No. US94/02401 filed Mar. 11, 1994), which is a continuation-in-part of U.S. patent application Ser. No. 08/030,644 filed Mar. 12, 1993, the disclosures of all of which are incorporated herein by reference.

Presently preferred BPI protein products include recombinantly-produced N-terminal fragments of BPI, especially those having a molecular weight of approximately between 21 to 25 kD such as rBPI$_{23}$, or dimeric forms of these N-terminal fragments (e.g., rBPI$_{42}$ dimer), or rBPI$_{21}$. Additionally, preferred BPI protein products include rBPI$_{50}$ and BPI-derived peptides.

The administration of BPI protein products is preferably accomplished with a pharmaceutical composition comprising a BPI protein product and a pharmaceutically acceptable diluent, adjuvant, or carder. The BPI protein product may be administered without or in conjunction with known surfactants, other chemotherapeutic agents or additional known anti-microbial agents. One pharmaceutical composition containing BPI protein products (e.g., rBPI$_{50}$, rBPI$_{23}$) comprises the BPI protein product at a concentration of 1 mg/ml in citrate buffered saline (5 or 20 mM citrate, 150 mM NaCl, pH 5.0) comprising 0.1% by weight of poloxamer 188 (Pluronic F-68, BASF Wyandotte, Parsippany, N.J.) and 0.002% by weight of polysorbate 80 (Tween 80, ICI Americas Inc., Wilmington, Del.). Another pharmaceutical composition containing BPI protein products (e.g., rBPI$_{21}$) comprises the BPI protein product at a concentration of 2 mg/ml in 5 mM citrate, 150 mM NaCl, 0.2% poloxamer 188 and 0.002% polysorbate 80. Such combinations are described in co-owned, co-pending PCT Application No. US94/01239 filed Feb. 2, 1994, which corresponds to U.S. patent application Ser. No. 08/190,869 filed Feb. 2, 1994 and U.S. patent application Ser. No. 08/012,360 filed Feb. 2, 1993, the disclosures of all of which are incorporated herein by reference.

Other aspects and advantages of the present invention will be understood upon consideration of the following illustrative examples. Example 1 addresses the effects of BPI protein product administration on tissue leukosequestration and edema in burned rats. Example 2 addresses the effects of BPI protein product administration on bacterial translocation in burned mice.

EXAMPLE 1

EFFECT OF BPI PROTEIN PRODUCT ADMINISTRATION ON PMN ACTIVITY, SEQUESTRATION AND TISSUE EDEMA IN A BURNED RAT MODEL

The effect of BPI protein product treatment on postburn PMN respiratory burst activity, PMN leukosequestration and tissue edema in multiple tissues was evaluated in a burned rat model.

Male Wistar rats (200–300 gm) were anesthetized by intraperitoneal (i.p.) injection with a dose of 2 mg/100 g Nembutal® (Abbott Labs, N. Chicago, Ill.) and 0.4 mg/100 g Diazepam® (Elkins and Sinn, Cherry Hill, N.J.), and were shaved and depilated. The animals underwent tracheostomy with a polyethylene tube (¾ inch, 3 mm internal diameter) and were allowed to breathe spontaneously through the tracheostomy tube. The femoral or internal jugular vein was then cannulated by cutdown with polyethylene tubing (PE 50). Animals were maintained normothermic with a 37° C. heating pad. The rats were divided into a control group, an untreated burned group, and a BPI-treated burned group (5 rats in each group). Rats in the BPI-treated group were administered 2 mg/kg of recombinant BPI rBPI$_{23}$ immediately preburn, via intravenous injection.

Animals were burned by applying a convex stainless steel template (approximately 8 cm×5.8 cm×0.4 cm) that had been heated to 250° C. to the depilated dorsum of the anesthetized animal for 7 sec. The template produced a burn covering approximately 17% of the total body surface area (TBSA). Slight changes in template size were utilized for various body weights of the animals to produce burn sizes of a uniform 17% of calculated TBSA. The animal was resuscitated with 20 mL of saline i.p. immediately postburn.

Leukosequestration in lung, liver, spleen, gut, skin, muscle, kidney and brain at 5 hours postburn was studied using radiolabeled PMNs and erythrocytes. Immediately before burn, 1 mL of venous blood was drawn from the indwelling catheter into a heparinized tube for preparation of the cells. The PMN fraction was obtained by centrifuging diluted whole blood on a two-step Percoll® density gradient (Pharmacia Biotech, Sollentuna, Sweden). The PMN fraction was retrieved and labelled with $^{111}$In by mixing 1 mL of the cell suspension (0.10 to 3×10$^6$ cells) with 1–5 μL of $^{111}$In indium oxide solution (37 MBq/mL, Amersham International plc, Amersham, UK) and incubating for 30 min. at room temperature. Cells were washed twice and resuspended in 1 mL of PBS, and their radioactivity was measured in a gamma counter before they were reinjected via the venous catheter.

Erythrocyte labelling was performed on the leukocyte-free fraction obtained through the separation procedure described above. Cells were suspended in 1 mL of Hanks' Balanced Salt Solution (HBSS) and incubated with 20μL of $^{51}$Cr sodium chromate solution (37 MBq/mL, Amersham) for 30 min. at room temperature. The radiolabelled erythrocytes were washed twice, pooled with the radiolabelled PMNs, and reinjected 4.5 hours after the burn was performed.

At 5 hours postburn, a 1 mL blood sample was drawn from the venous catheter, animals were immediately sacrificed by rapid installation of 5 mL glutaraldehyde (2.5% in 0.05 M sodium cacodylate) through the tracheostomy, and their viscera were immediately procured and assayed. The radioactivity (dpm, disintegrations per minute) of the blood samples, the excised lungs, kidneys, spleen and sections of liver, intestine, skeletal muscle, non-burned skin and brain were measured. The leukocyte transit time factors were calculated as a measure of tissue-specific leukocyte sequestration, according to the following formula: Transit factor = (Regional $^{111}$In dpm × $^{51}$Cr dpm/mL venous blood)/(Regional $^{51}$Cr activity × $^{111}$In activity/mL venous blood).

Tissue edema was measured by determining extravasation of $^{125}$I-labelled albumin in tissue. 1–10 μL of $^{125}$I-labelled human albumin (37 MBq/mL, Amersham) was injected at the same time as the radiolabelled cells. The ratio of albumin to erythrocytes in the various tissues and organs was calculated in the same manner as for the leukocytes and was used as a measure of tissue edema.

Peripheral blood PMN respiratory burst was also measured by quantifying the intracellular content of $H_2O_2$, using 2,7-dichlorodihydrofluorescein diacetate (DCFH-DA), which crosses the cell membrane and changes its fluorescence emission spectrum after reacting with intracellular $H_2O_2$. Blood was drawn from the vena cava into a heparinized tube. A 100 μL aliquot of blood was diluted with 850 μL of PBS, and 8 μL of 5 mM DCFH-DA (Molecular Probes, Eugene, Oreg.) was added. Following 15 min. of incubation, 30 μL of 1.67 mg/mL LDS-751 (Exciton, Dayton, Ohio) was added just prior to flow cytometric analysis of cell fluorescence, in order to label the nuclei of living cells and permit their identification without interference from erythrocytes. For FMLP-induced reactive oxygen species measurement, DCFH-DA labeled samples were incubated with 25 μL of 20 mM F-met-leu-phe (FLMP, Sigma, St. Louis, Mo.) at 37° C. for 30 min. Samples were analyzed at 0 and 30 min. on a Becton-Dickinson FACStar dual-channel flow cytometer (Becton-Dickinson Immunocytometry Systems, San Jose, Calif.). The instrument was set up to measure linear forward scatter (FSC), which is a measure of particle size, linear 90° light scatter (SSC), which is a measure of cell granularity, and green fluorescence at 535 nm (corresponding to DCFH) and red fluorescence (corresponding to LDS-751) at 620 nm. Nucleated (red fluorescent) cells were analyzed for PMN mean channel fluorescence at 535 nm.

For the respiratory burst experiments, statistical comparisons between experimental groups were performed by multiple ANOVA and the t-test (Instat® software, San Diego, Calif.), with significance at $p<0.05$. For the leukosequestration and tissue edema studies, the results obtained for the various organs in the control and burned groups of animals were compared using the Mann-Whitney U-test for non-parametric data, with significance at $p<0.05$, in a two-tailed distribution. All data are displayed using the mean and standard error of the mean.

Accumulation of PMNs in the lung can also be estimated by measuring MPO in lung tissue. At various time points after burn injury, rats may be killed by cervical dislocation. The chest cavity is then opened and the lungs are flushed with saline via cardiac puncture. Lungs are harvested, weighed and snap frozen at −70° C. for subsequent batch processing. MPO is assayed by measuring the $H_2O_2$-dependent oxidation of o-dianisidine as follows. Lung tissue samples are homogenized, suspended in 0.45% saline, and centrifuged. The supernatant is discarded and the pellet resuspended in 1 mL/50 mg tissue of 0.05 M potassium phosphate buffer, pH 6.0, containing 0.55 mixed trimethylammonium bromide (MTAB, Sigma, St. Louis, Mo.), followed by a three-time freeze-thaw cycle and additional sonication. After centrifugation at 4° C., 0.033 mL of the supernatant is mixed with 0.967 mL of 0.05 M potassium phosphate buffer, pH 6.0, containing 0.167 mg/mL o-dianisidine hydrochloride (Sigma, St. Louis, Mo.), and 0.4 μL/mL of 3% $H_2O_2$. Absorbance is immediately measured at 460 nm (DU-7 Spectrophotometer, Beckmann Instruments, Fullerton, Calif.). A standard curve is created using human MPO (Sigma, St. Louis, Mo.). Certain factors which can interfere with the assay can be eliminated by heating the tissues, since MPO is a heat-stable enzyme.

Mortality after the 17% TBSA burn injury ranges from 20% to 50%. Previous studies showed that increasing the amount of resuscitation fluid did not improve animal survival. Tissues from animals which expired spontaneously were not utilized for obtaining any of the data in these studies. In general, after burn injury animals develop pronounced metabolic acidosis which persists through at least 12 hours postburn but returns to normal by 18 hours postburn. MPO is typically elevated in lungs at 9 hours postburn, and marked PMN influx into lung tissues can be seen on histologic examination.

Results of this experiment showed that peripheral blood PMN respiratory burst activity was increased at 5 hours postburn ($p<0.05$) in the untreated burned animals, compared to control animals. Treatment with BPI protein product had no significant effect on PMN respiratory burst activity. Tissue edema was not observed in either burned or control (nonburned) animals.

Radioisotope studies showed significantly higher ($p<0.05$) PMN sequestration in lung, gut, kidney, skin and brain tissues at 5 hours postburn in the untreated, burned animals as compared to the control animals. Administration of BPI protein product significantly reduced PMN sequestration ($p<0.05$) in the lung and liver of the burned animals. The PMN flux values (ratio of tissue PMNs/erythrocytes), the indicator of PMN sequestration, are displayed below in Table 1.

|  | Lung | Liver | Skin | Gut |
| --- | --- | --- | --- | --- |
| Control | 1.842 ± 0.526 | 7.200 ± 2.258 | 3.510 ± 1.135 | 3.258 + 0.907 |
| Burn | 8.024 ± 1.417 | 17.108 ± 2.907 | 10.766 ± 2.368 | 10.344 + 1.851 |
| Burn-BPI | 2.572 ± 10.556 | 7.718 ± 2.383 | 8.436 ± 2.917 | 7.362 + 3.516 |

*P < 0.05 compared to control samples, ANOVA and t-test.

The data in Table 1 show that the burn injury in these rats resulted in accumulation of PMNs in multiple tissues, and that this PMN accumulation was effectively blocked in lung and liver by administration of BPI protein product preburn. Considering that sequestration of metabolically active PMNs is believed to induce tissue injury, therapies such as BPI protein product which block postburn leukosequestration are expected to improve clinical outcomes by limiting remote tissue injury.

EXAMPLE 2

EFFECT OF BPI PROTEIN PRODUCT ADMINISTRATION ON BACTERIAL TRANSLOCATION IN A BURNED MOUSE MODEL

The effect of BPI protein product treatment on the incidence of bacterial translocation (as measured by bacterial accumulation in mesenteric lymph nodes) was evaluated in a burned mouse model. Burn injury has been shown to induce bacterial translocation from the gut in multiple animal models. Etiological factors of translocation may include ischemia/reperfusion phenomena, including the release of inflammatory cytokines and other mediators, and cytotoxic effects mediated by endotoxin (LPS); however, the role of these factors in bacterial translocation has not been well defined.

Female CF-1 mice received a severe 32% TBSA full-thickness scald burn. All animals received a total of 1 mL saline i.p. immediately postburn for fluid resuscitation. BPI-treated burned animals received 10 mg/kg rBPI$_{23}$ in saline by i.p. injection, immediately postburn and at 3 and 6 hours postburn. Control animals received i.p. saline only. At 24 hours postburn, each animal's mesenteric lymph nodes were harvested in a sterile manner, homogenized, plated on brain-heart-infusion agar and incubated at 37° C. If an animal's lymph nodes showed any bacterial growth at 48 hours, that animal was scored as positive (+).

Data are displayed below in Table 2. The data show that burned mice treated with rBPI$_{23}$ had a significant (p=0.011) decrease in the incidence of bacterial translocation compared to burned, saline-treated controls.

| Group | No. Mice | #MLN (+) | #MLN (−) | Incidence of Bacterial Translocation |
|---|---|---|---|---|
| No Burn | 22 | 0 | 22 | 0% |
| Burned-Saline Rx | 18 | 10 | 8 | 55.5% |
| Burned-BPI Rx | 17 | 2 | 15 | 11.8% |

Postburn administration of BPI protein product was demonstrated to reduce the incidence of bacterial translocation following severe burn injury in mice. BPI protein product may also act to increase clearance and killing of bacteria by host defenses, after the bacteria have migrated to the mesenteric tissues. Thus, BPI protein products are expected to be valuable in the treatment of severe burn injury.

In unrelated experiments, rats were burned and infected immediately with a certain dose and strain of *Klebsiella pneumoniae* but were not treated until the fourth day after burn and simultaneous infection with BPI in combination with either lipid X or monophosphoryl lipid A (MPLA). No reduction of mortality under these conditions was observed in the lipid X- or MPLA-treated mice with or without BPI. Such results were not surprising given the infection load, the late administration of BPI, the lack of concurrent antibiotic treatment, and the relative resistance of Klebsiella species to in vitro BPI killing. In contrast to such conditions, BPI protein product therapy is generally expected to be initiated soon after burn injury and prior to the development of infection, and has been shown to be effective under these conditions as illustrated above in Examples 1–2.

Numerous modifications and variations of the above-described invention are expected to occur to those of skill in the art. Accordingly, only such limitations as appear in the appended claims should be placed thereon.

What is claimed is:

1. A method of reducing leukosequestration associated with burn injuries comprising the step of administering a therapeutically effective amount of a bactericidal/permeability-increasing (BPI) protein product to a subject suffering from the effects of a burn injury.

2. The method of claim 1 wherein the BPI protein product is an approximately 25 kilodalton amino-terminal fragment of BPI protein.

3. The method of claim 1 wherein the BPI protein product is rBPI$_{23}$ or a dimeric form thereof.

4. The method of claim 1 wherein the BPI protein product is rBPI$_{21}$.

5. The method of claim 1 further comprising the step of administering an antibiotic or anti-fungal agent.

6. A method of reducing bacterial translocation from gut that is associated with burn injuries, comprising the step of administering a therapeutically effective amount of a bactericidal/permeability-increasing (BPI)protein product to a subject suffering from the effects of a burn injury.

7. The method of claim 6 wherein the BPI protein product is an approximately 25 kiladalton amino-terminal fragment of BPI protein.

8. The method of claim 6 wherein the BPI protein product is $rBPI_{23}$ or a dimeric form thereof.

9. The method of claim 6 wherein the BPI protein product is $rBPI_{21}$.

10. The method of claim 6 further comprising the step of administering an antibiotic or anti-fungal agent.

* * * * *

UNITED STATES PATENT AND TRADEMARK OFFICE
CERTIFICATE OF CORRECTION

PATENT NO.    : 5,494,896
DATED         : February 27, 1996
INVENTOR(S)   : John F. Hansbrough It is certified that error appears in the above-identified patent and that said Letters Patent is hereby corrected as shown below:

Column 9, line 40, "carder" should be --carrier--.

Column 22, line 1, "kiladalton" should be --kilodalton--.

Signed and Sealed this

Twenty-fifth Day of June, 1996

Attest:

BRUCE LEHMAN

*Attesting Officer*    *Commissioner of Patents and Trademarks*

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1813 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 31..1491

( i x ) FEATURE:
        ( A ) NAME/KEY: mat_peptide
        ( B ) LOCATION: 124..1491

( i x ) FEATURE:
        ( A ) NAME/KEY: misc_feature
        ( D ) OTHER INFORMATION: "rBPI"

( x i ) SEQUENCE DESCRIPTION: SEQ ID NO:1:

```
CAGGCCTTGA GGTTTTGGCA GCTCTGGAGG ATG AGA GAG AAC ATG GCC AGG GGC        54
                                 Met Arg Glu Asn Met Ala Arg Gly
                                 -31 -30                      -25

CCT TGC AAC GCG CCG AGA TGG GTG TCC CTG ATG GTG CTC GTC GCC ATA        102
Pro Cys Asn Ala Pro Arg Trp Val Ser Leu Met Val Leu Val Ala Ile
            -20             -15                      -10

GGC ACC GCC GTG ACA GCG GCC GTC AAC CCT GGC GTG GTG GTC AGG ATC        150
Gly Thr Ala Val Thr Ala Ala Val Asn Pro Gly Val Val Val Arg Ile
        -5                      1                5
```

| | | | | | | | | | | | | | | | | |
|---|---|---|---|---|---|---|---|---|---|---|---|---|---|---|---|---|
| TCC | CAG | AAG | GGC | CTG | GAC | TAC | GCC | AGC | CAG | CAG | GGG | ACG | GCC | GCT | CTG | 198 |
| Ser | Gln | Lys | Gly | Leu | Asp | Tyr | Ala | Ser | Gln | Gln | Gly | Thr | Ala | Ala | Leu | |
| 10 | | | | 15 | | | | | 20 | | | | | | 25 | |
| CAG | AAG | GAG | CTG | AAG | AGG | ATC | AAG | ATT | CCT | GAC | TAC | TCA | GAC | AGC | TTT | 246 |
| Gln | Lys | Glu | Leu | Lys | Arg | Ile | Lys | Ile | Pro | Asp | Tyr | Ser | Asp | Ser | Phe | |
| | | | | 30 | | | | | 35 | | | | | 40 | | |
| AAG | ATC | AAG | CAT | CTT | GGG | AAG | GGG | CAT | TAT | AGC | TTC | TAC | AGC | ATG | GAC | 294 |
| Lys | Ile | Lys | His | Leu | Gly | Lys | Gly | His | Tyr | Ser | Phe | Tyr | Ser | Met | Asp | |
| | | | 45 | | | | | 50 | | | | | 55 | | | |
| ATC | CGT | GAA | TTC | CAG | CTT | CCC | AGT | TCC | CAG | ATA | AGC | ATG | GTG | CCC | AAT | 342 |
| Ile | Arg | Glu | Phe | Gln | Leu | Pro | Ser | Ser | Gln | Ile | Ser | Met | Val | Pro | Asn | |
| | | 60 | | | | | 65 | | | | | 70 | | | | |
| GTG | GGC | CTT | AAG | TTC | TCC | ATC | AGC | AAC | GCC | AAT | ATC | AAG | ATC | AGC | GGG | 390 |
| Val | Gly | Leu | Lys | Phe | Ser | Ile | Ser | Asn | Ala | Asn | Ile | Lys | Ile | Ser | Gly | |
| | 75 | | | | | 80 | | | | | 85 | | | | | |
| AAA | TGG | AAG | GCA | CAA | AAG | AGA | TTC | TTA | AAA | ATG | AGC | GGC | AAT | TTT | GAC | 438 |
| Lys | Trp | Lys | Ala | Gln | Lys | Arg | Phe | Leu | Lys | Met | Ser | Gly | Asn | Phe | Asp | |
| 90 | | | | | 95 | | | | | 100 | | | | | 105 | |
| CTG | AGC | ATA | GAA | GGC | ATG | TCC | ATT | TCG | GCT | GAT | CTG | AAG | CTG | GGC | AGT | 486 |
| Leu | Ser | Ile | Glu | Gly | Met | Ser | Ile | Ser | Ala | Asp | Leu | Lys | Leu | Gly | Ser | |
| | | | | 110 | | | | | 115 | | | | | 120 | | |
| AAC | CCC | ACG | TCA | GGC | AAG | CCC | ACC | ATC | ACC | TGC | TCC | AGC | TGC | AGC | AGC | 534 |
| Asn | Pro | Thr | Ser | Gly | Lys | Pro | Thr | Ile | Thr | Cys | Ser | Ser | Cys | Ser | Ser | |
| | | | 125 | | | | | 130 | | | | | 135 | | | |
| CAC | ATC | AAC | AGT | GTC | CAC | GTG | CAC | ATC | TCA | AAG | AGC | AAA | GTC | GGG | TGG | 582 |
| His | Ile | Asn | Ser | Val | His | Val | His | Ile | Ser | Lys | Ser | Lys | Val | Gly | Trp | |
| | | 140 | | | | | 145 | | | | | 150 | | | | |
| CTG | ATC | CAA | CTC | TTC | CAC | AAA | AAA | ATT | GAG | TCT | GCG | CTT | CGA | AAC | AAG | 630 |
| Leu | Ile | Gln | Leu | Phe | His | Lys | Lys | Ile | Glu | Ser | Ala | Leu | Arg | Asn | Lys | |
| | 155 | | | | | 160 | | | | | 165 | | | | | |
| ATG | AAC | AGC | CAG | GTC | TGC | GAG | AAA | GTG | ACC | AAT | TCT | GTA | TCC | TCC | AAG | 678 |
| Met | Asn | Ser | Gln | Val | Cys | Glu | Lys | Val | Thr | Asn | Ser | Val | Ser | Ser | Lys | |
| 170 | | | | | 175 | | | | | 180 | | | | | 185 | |
| CTG | CAA | CCT | TAT | TTC | CAG | ACT | CTG | CCA | GTA | ATG | ACC | AAA | ATA | GAT | TCT | 726 |
| Leu | Gln | Pro | Tyr | Phe | Gln | Thr | Leu | Pro | Val | Met | Thr | Lys | Ile | Asp | Ser | |
| | | | | 190 | | | | | 195 | | | | | 200 | | |
| GTG | GCT | GGA | ATC | AAC | TAT | GGT | CTG | GTG | GCA | CCT | CCA | GCA | ACC | ACG | GCT | 774 |
| Val | Ala | Gly | Ile | Asn | Tyr | Gly | Leu | Val | Ala | Pro | Pro | Ala | Thr | Thr | Ala | |
| | | | 205 | | | | | 210 | | | | | 215 | | | |
| GAG | ACC | CTG | GAT | GTA | CAG | ATG | AAG | GGG | GAG | TTT | TAC | AGT | GAG | AAC | CAC | 822 |
| Glu | Thr | Leu | Asp | Val | Gln | Met | Lys | Gly | Glu | Phe | Tyr | Ser | Glu | Asn | His | |
| | | 220 | | | | | 225 | | | | | 230 | | | | |
| CAC | AAT | CCA | CCT | CCC | TTT | GCT | CCA | CCA | GTG | ATG | GAG | TTT | CCC | GCT | GCC | 870 |
| His | Asn | Pro | Pro | Pro | Phe | Ala | Pro | Pro | Val | Met | Glu | Phe | Pro | Ala | Ala | |
| | 235 | | | | | 240 | | | | | 245 | | | | | |
| CAT | GAC | CGC | ATG | GTA | TAC | CTG | GGC | CTC | TCA | GAC | TAC | TTC | TTC | AAC | ACA | 918 |
| His | Asp | Arg | Met | Val | Tyr | Leu | Gly | Leu | Ser | Asp | Tyr | Phe | Phe | Asn | Thr | |
| 250 | | | | 255 | | | | | 260 | | | | | 265 | | |
| GCC | GGG | CTT | GTA | TAC | CAA | GAG | GCT | GGG | GTC | TTG | AAG | ATG | ACC | CTT | AGA | 966 |
| Ala | Gly | Leu | Val | Tyr | Gln | Glu | Ala | Gly | Val | Leu | Lys | Met | Thr | Leu | Arg | |
| | | | | 270 | | | | | 275 | | | | | 280 | | |
| GAT | GAC | ATG | ATT | CCA | AAG | GAG | TCC | AAA | TTT | CGA | CTG | ACA | ACC | AAG | TTC | 1014 |
| Asp | Asp | Met | Ile | Pro | Lys | Glu | Ser | Lys | Phe | Arg | Leu | Thr | Thr | Lys | Phe | |
| | | | 285 | | | | | 290 | | | | | 295 | | | |
| TTT | GGA | ACC | TTC | CTA | CCT | GAG | GTG | GCC | AAG | AAG | TTT | CCC | AAC | ATG | AAG | 1062 |
| Phe | Gly | Thr | Phe | Leu | Pro | Glu | Val | Ala | Lys | Lys | Phe | Pro | Asn | Met | Lys | |
| | | 300 | | | | | 305 | | | | | 310 | | | | |
| ATA | CAG | ATC | CAT | GTC | TCA | GCC | TCC | ACC | CCG | CCA | CAC | CTG | TCT | GTG | CAG | 1110 |
| Ile | Gln | Ile | His | Val | Ser | Ala | Ser | Thr | Pro | Pro | His | Leu | Ser | Val | Gln | |
| | 315 | | | | | 320 | | | | | 325 | | | | | |

| | | | | | | | | | | | | | | | |
|---|---|---|---|---|---|---|---|---|---|---|---|---|---|---|---|
|CCC|ACC|GGC|CTT|ACC|TTC|TAC|CCT|GCC|GTG|GAT|GTC|CAG|GCC|TTT|GCC|
|Pro|Thr|Gly|Leu|Thr|Phe|Tyr|Pro|Ala|Val|Asp|Val|Gln|Ala|Phe|Ala|
|330| | | |335| | | | |340| | | | |345| |

1158

|GTC|CTC|CCC|AAC|TCC|TCC|CTG|GCT|TCC|CTC|TTC|CTG|ATT|GGC|ATG|CAC|
|---|---|---|---|---|---|---|---|---|---|---|---|---|---|---|---|
|Val|Leu|Pro|Asn|Ser|Ser|Leu|Ala|Ser|Leu|Phe|Leu|Ile|Gly|Met|His|
| | | | |350| | | | |355| | | | |360| |

1206

|ACA|ACT|GGT|TCC|ATG|GAG|GTC|AGC|GCC|GAG|TCC|AAC|AGG|CTT|GTT|GGA|
|---|---|---|---|---|---|---|---|---|---|---|---|---|---|---|---|
|Thr|Thr|Gly|Ser|Met|Glu|Val|Ser|Ala|Glu|Ser|Asn|Arg|Leu|Val|Gly|
| | | |365| | | | |370| | | | |375| | |

1254

|GAG|CTC|AAG|CTG|GAT|AGG|CTG|CTC|CTG|GAA|CTG|AAG|CAC|TCA|AAT|ATT|
|---|---|---|---|---|---|---|---|---|---|---|---|---|---|---|---|
|Glu|Leu|Lys|Leu|Asp|Arg|Leu|Leu|Leu|Glu|Leu|Lys|His|Ser|Asn|Ile|
| | |380| | | |385| | | |390| | | | | |

1302

|GGC|CCC|TTC|CCG|GTT|GAA|TTG|CTG|CAG|GAT|ATC|ATG|AAC|TAC|ATT|GTA|
|---|---|---|---|---|---|---|---|---|---|---|---|---|---|---|---|
|Gly|Pro|Phe|Pro|Val|Glu|Leu|Leu|Gln|Asp|Ile|Met|Asn|Tyr|Ile|Val|
| |395| | | |400| | | | |405| | | | | |

1350

|CCC|ATT|CTT|GTG|CTG|CCC|AGG|GTT|AAC|GAG|AAA|CTA|CAG|AAA|GGC|TTC|
|---|---|---|---|---|---|---|---|---|---|---|---|---|---|---|---|
|Pro|Ile|Leu|Val|Leu|Pro|Arg|Val|Asn|Glu|Lys|Leu|Gln|Lys|Gly|Phe|
|410| | | | |415| | | | |420| | | | |425|

1398

|CCT|CTC|CCG|ACG|CCG|GCC|AGA|GTC|CAG|CTC|TAC|AAC|GTA|GTG|CTT|CAG|
|---|---|---|---|---|---|---|---|---|---|---|---|---|---|---|---|
|Pro|Leu|Pro|Thr|Pro|Ala|Arg|Val|Gln|Leu|Tyr|Asn|Val|Val|Leu|Gln|
| | | |430| | | | |435| | | | |440| | |

1446

|CCT|CAC|CAG|AAC|TTC|CTG|CTG|TTC|GGT|GCA|GAC|GTT|GTC|TAT|AAA| |
|---|---|---|---|---|---|---|---|---|---|---|---|---|---|---|---|
|Pro|His|Gln|Asn|Phe|Leu|Leu|Phe|Gly|Ala|Asp|Val|Val|Tyr|Lys| |
| | | |445| | | | |450| | | | |455| | |

1491

| | | | |
|---|---|---|---|
|TGAAGGCACC|AGGGGTGCCG|GGGGCTGTCA|GCCGCACCTG TTCCTGATGG GCTGTGGGGC|
|ACCGGCTGCC|TTTCCCCAGG|GAATCCTCTC|CAGATCTTAA CCAAGAGCCC CTTGCAAACT|
|TCTTCGACTC|AGATTCAGAA|ATGATCTAAA|CACGAGGAAA CATTATTCAT TGGAAAAGTG|
|CATGGTGTGT|ATTTTAGGGA|TTATGAGCTT|CTTTCAAGGG CTAAGGCTGC AGAGATATTT|
|CCTCCAGGAA|TCGTGTTTCA|ATTGTAACCA|AGAAATTTCC ATTTGTGCTT CATGAAAAAA|
|AACTTCTGGT|TTTTTTCATG|TG| |

1551
1611
1671
1731
1791
1813

( 2 ) INFORMATION FOR SEQ ID NO:2:

( i ) SEQUENCE CHARACTERISTICS:
    ( A ) LENGTH: 487 amino acids
    ( B ) TYPE: amino acid
    ( D ) TOPOLOGY: linear ( i i ) MOLECULE TYPE: protein ( x i ) SEQUENCE DESCRIPTION: SEQ ID NO:2:

|Met|Arg|Glu|Asn|Met|Ala|Arg|Gly|Pro|Cys|Asn|Ala|Pro|Arg|Trp|Val|
|---|---|---|---|---|---|---|---|---|---|---|---|---|---|---|---|
|-31| |-30| | | |-25| | | |-20| | | | | |

|Ser|Leu|Met|Val|Leu|Val|Ala|Ile|Gly|Thr|Ala|Val|Thr|Ala|Ala|Val|
|---|---|---|---|---|---|---|---|---|---|---|---|---|---|---|---|
|-15| | | |-10| | | | |-5| | | | | |1|

|Asn|Pro|Gly|Val|Val|Val|Arg|Ile|Ser|Gln|Lys|Gly|Leu|Asp|Tyr|Ala|
|---|---|---|---|---|---|---|---|---|---|---|---|---|---|---|---|
| | | |5| | | | |10| | | | |15| | |

|Ser|Gln|Gln|Gly|Thr|Ala|Ala|Leu|Gln|Lys|Glu|Leu|Lys|Arg|Ile|Lys|
|---|---|---|---|---|---|---|---|---|---|---|---|---|---|---|---|
| | |20| | | | |25| | | | |30| | | |

|Ile|Pro|Asp|Tyr|Ser|Asp|Ser|Phe|Lys|Ile|Lys|His|Leu|Gly|Lys|Gly|
|---|---|---|---|---|---|---|---|---|---|---|---|---|---|---|---|
| |35| | | | |40| | | | |45| | | | |

|His|Tyr|Ser|Phe|Tyr|Ser|Met|Asp|Ile|Arg|Glu|Phe|Gln|Leu|Pro|Ser|
|---|---|---|---|---|---|---|---|---|---|---|---|---|---|---|---|
|50| | | | |55| | | | |60| | | | |65|

|Ser|Gln|Ile|Ser|Met|Val|Pro|Asn|Val|Gly|Leu|Lys|Phe|Ser|Ile|Ser|
|---|---|---|---|---|---|---|---|---|---|---|---|---|---|---|---|
| | | |70| | | | |75| | | | |80| | |

|Asn|Ala|Asn|Ile|Lys|Ile|Ser|Gly|Lys|Trp|Lys|Ala|Gln|Lys|Arg|Phe|
|---|---|---|---|---|---|---|---|---|---|---|---|---|---|---|---|
| | | |85| | | | |90| | | | |95| | |

| | | | | | | | | | | | | | | |
|---|---|---|---|---|---|---|---|---|---|---|---|---|---|---|
| Leu | Lys | Met 100 | Ser | Gly | Asn | Phe | Asp 105 | Leu | Ser | Ile | Glu | Gly 110 | Met | Ser | Ile |
| Ser | Ala 115 | Asp | Leu | Lys | Leu | Gly 120 | Ser | Asn | Pro | Thr | Ser 125 | Gly | Lys | Pro | Thr |
| Ile 130 | Thr | Cys | Ser | Ser | Cys 135 | Ser | Ser | His | Ile | Asn 140 | Ser | Val | His | Val | His 145 |
| Ile | Ser | Lys | Ser | Lys 150 | Val | Gly | Trp | Leu | Ile 155 | Gln | Leu | Phe | His | Lys 160 | Lys |
| Ile | Glu | Ser | Ala 165 | Leu | Arg | Asn | Lys | Met 170 | Asn | Ser | Gln | Val | Cys 175 | Glu | Lys |
| Val | Thr | Asn 180 | Ser | Val | Ser | Ser | Lys 185 | Leu | Gln | Pro | Tyr | Phe 190 | Gln | Thr | Leu |
| Pro | Val 195 | Met | Thr | Lys | Ile | Asp 200 | Ser | Val | Ala | Gly | Ile 205 | Asn | Tyr | Gly | Leu |
| Val 210 | Ala | Pro | Pro | Ala | Thr 215 | Thr | Ala | Glu | Thr | Leu 220 | Asp | Val | Gln | Met | Lys 225 |
| Gly | Glu | Phe | Tyr | Ser 230 | Glu | Asn | His | His | Asn 235 | Pro | Pro | Pro | Phe | Ala 240 | Pro |
| Pro | Val | Met | Glu 245 | Phe | Pro | Ala | Ala | His 250 | Asp | Arg | Met | Val | Tyr 255 | Leu | Gly |
| Leu | Ser | Asp 260 | Tyr | Phe | Phe | Asn | Thr 265 | Ala | Gly | Leu | Val | Tyr 270 | Gln | Glu | Ala |
| Gly | Val 275 | Leu | Lys | Met | Thr | Leu 280 | Arg | Asp | Asp | Met | Ile 285 | Pro | Lys | Glu | Ser |
| Lys 290 | Phe | Arg | Leu | Thr | Thr 295 | Lys | Phe | Phe | Gly | Thr 300 | Phe | Leu | Pro | Glu | Val 305 |
| Ala | Lys | Lys | Phe | Pro 310 | Asn | Met | Lys | Ile | Gln 315 | Ile | His | Val | Ser | Ala 320 | Ser |
| Thr | Pro | Pro | His 325 | Leu | Ser | Val | Gln | Pro 330 | Thr | Gly | Leu | Thr | Phe 335 | Tyr | Pro |
| Ala | Val | Asp 340 | Val | Gln | Ala | Phe | Ala 345 | Val | Leu | Pro | Asn | Ser 350 | Ser | Leu | Ala |
| Ser | Leu 355 | Phe | Leu | Ile | Gly | Met 360 | His | Thr | Thr | Gly | Ser 365 | Met | Glu | Val | Ser |
| Ala 370 | Glu | Ser | Asn | Arg | Leu 375 | Val | Gly | Glu | Leu | Lys 380 | Leu | Asp | Arg | Leu | Leu 385 |
| Leu | Glu | Leu | Lys | His 390 | Ser | Asn | Ile | Gly | Pro 395 | Phe | Pro | Val | Glu | Leu 400 | Leu |
| Gln | Asp | Ile | Met 405 | Asn | Tyr | Ile | Val | Pro 410 | Ile | Leu | Val | Leu | Pro 415 | Arg | Val |
| Asn | Glu | Lys 420 | Leu | Gln | Lys | Gly | Phe 425 | Pro | Leu | Pro | Thr | Pro 430 | Ala | Arg | Val |
| Gln | Leu 435 | Tyr | Asn | Val | Val | Leu 440 | Gln | Pro | His | Gln | Asn 445 | Phe | Leu | Leu | Phe |
| Gly 450 | Ala | Asp | Val | Val | Tyr 455 | Lys | | | | | | | | | |